(12) United States Patent
Dvornic et al.

(10) Patent No.: US 7,141,437 B2
(45) Date of Patent: Nov. 28, 2006

(54) SOLID-STATE COLORIMETRIC BIOSENSORS COMPRISED OF DENDRITIC POLYMER NETWORKS

(75) Inventors: Petar R. Dvornic, Midland, MI (US); Steven N. Kaganove, Midland, MI (US); Abhijit Sarkar, Midland, MI (US)

(73) Assignee: Michigan Molecular Institute, Midland, MI (US)

( * ) Notice: Subject to any disclaimer, the term of this patent is extended or adjusted under 35 U.S.C. 154(b) by 0 days.

(21) Appl. No.: 10/712,739

(22) Filed: Nov. 13, 2003

(65) Prior Publication Data

US 2005/0106572 A1 May 19, 2005

(51) Int. Cl.
*G01N 33/547* (2006.01)
*G01N 33/532* (2006.01)
*G01N 21/63* (2006.01)
*G01N 21/78* (2006.01)

(52) U.S. Cl. .......... 436/532; 435/6; 436/164; 436/172; 436/531; 436/546; 436/501; 436/805

(58) Field of Classification Search ........ 436/546, 436/531, 532, 501, 164, 172, 805; 435/6
See application file for complete search history.

(56) References Cited

U.S. PATENT DOCUMENTS 5,622,872 A * 4/1997 Ribi ............... 436/518
6,001,556 A * 12/1999 Charych et al. ............ 435/5
6,022,748 A * 2/2000 Charych et al. .......... 436/527
2002/0192843 A1 12/2002 Kaganove et al.

OTHER PUBLICATIONS

L. Balogh et al, Macromolecules, vol. 32, pp. 1036-1042 (1999), Architectural Copolymers of PAMAM Dendrimers and Ionic Polyacetylenes.*
G. Sui et al., "Studies of a novel polymerizable amphiphilic dendrimer," *Colloids and Surfaces A: Physicochemical and Engineering Aspects*, vol. 171, (2000), pp. 185-197.
S. J. Lee et al., "Self-Assembly of Dendron Building Blocks With Topochemically Polymerizable Periphery," Polymer Preprints, vol. 43, No. 2, (2002), p. 450.

* cited by examiner

*Primary Examiner*—Mary E. Ceperley
(74) *Attorney, Agent, or Firm*—Price, Heneveld, Cooper, DeWitt & Litton, LLP (57) ABSTRACT

Solid-state colorimetric biosensors having sensory groups and interdendritic cross-linking segments of alternating conjugated double and triple bonds are prepared by intermolecular polymerization of diacetylene-functionalized dendritic polymer precursors. The polymerization process may be used to form solid films that are capable of indicating the presence of an analyte by a detectable change in color. The disclosed solid-state colorimetric biosensors may exhibit excellent stability at elevated temperatures and in the presence of organic solvents, and due to the dendritic architecture and high density of sensing functionality achieve high sensitivity to analytes.

27 Claims, 4 Drawing Sheets

SOLID-STATE COLORIMETRIC BIOSENSORS COMPRISED OF DENDRITIC POLYMER NETWORKS

BACKGROUND OF THE INVENTION

1. Field of the Invention

This invention is directed to colorimetric biosensors.

2. Description of Related Art

There has been a well-recognized need for fast, reliable and inexpensive analytical techniques that would be capable of detecting the presence of chemical and/or biological analytes. Although conventional analytical techniques, such as chromatography, mass spectrometry, titration, etc. can provide reliable results, these techniques are generally time consuming, expensive, performed in a laboratory at a fixed location, and are not easily portable or adaptable for portable use.

Various chemical and/or biological sensors have been developed to overcome some of the disadvantages of conventional instrumental methods of analyte detection. These are generally composed of two distinct functional components: a sensing element and a transducer. The sensing element chemically interacts with the analyte of interest to induce changes in some detectable physicochemical property, while the transducer detects theses changes and converts them into a measurable output signal.

Most chemical and/or biological sensors can be categorized into four main categories: optical, resistive, electrochemical or acoustic mass sensing devices. Among these, preferred are optical devices that generate colorimetric, fluorimetric or fluorescence depolarization signals, wherein the molecular recognition event triggers a detectable or noticeable color change that is observable by the naked eye and/or is quantifiable by optical absorption using spectroscopic instrumentation. A particularly promising step in this direction is a recently disclosed system of conjugated polymer vesicles that are bonded together with a polydiacetylene (PDA) backbone. When conjugated to biologically interactive carbohydrates such as sialic acid and ganglioside $G_{M1}$, the resulting highly colored polymerized vesicles exhibit visible binding-induced color changes in the presence of influenza virus and cholera toxin, respectively. Such color changes result from perturbation of PDA chain conformation and the extent of uninterrupted conjugation, which are typically caused by heat, interactions with reagents (including analytes), changes in pH, or mechanical stress.

Figure 1:
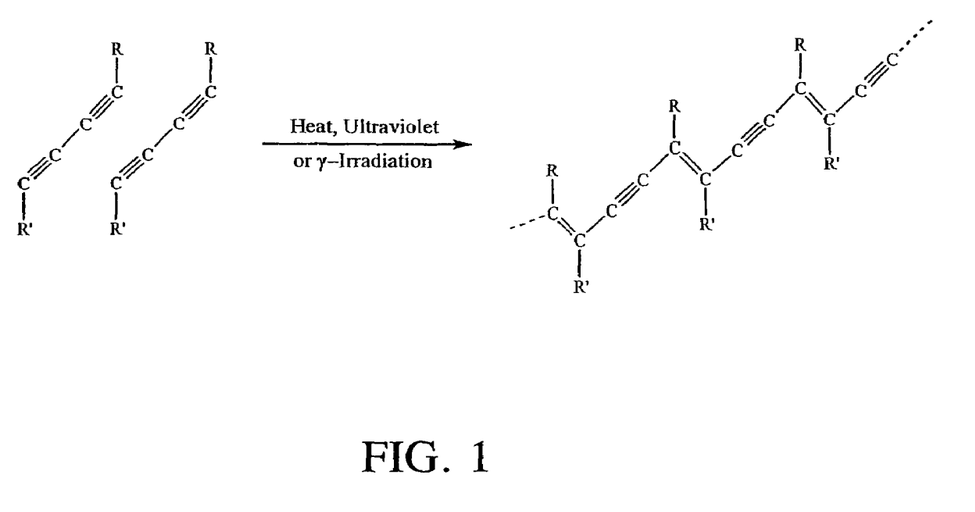
FIG. 1 is a schematic representation of diacetylene topochemical polymerization.

Diacetylenes are rather unusual among various classes of well-known polymerizable organic functional groups in that a highly ordered state is required for their polymerization to occur. In practice their polymerization has been achieved in solid state crystal lattices, Langmuir-Blodgett (LB) films, self-assembled monolayers (SAM) or vesicles. This, usually referred to as "topochemical polymerization," is typically initiated by heat or irradiation from an ultraviolet or gamma radiation source and proceeds by repeated 1,4-addition of diacetylene monomers in a geometrically constrained polymerization medium, as illustrated in FIG. 1. The resulting polymers have highly conjugated segments of alternating double and triple bonds along the backbone, and are usually highly colored. For example, in the case of polymerized vesicles, the predominant colors are blue, red or violet.

However, the reported PDA-vesicle system has the following limitations. First, since vesicle formation is based on self-assembly of a large number of small molecules, molecular architecture cannot be controlled directly, resulting in a variety of different shapes and sizes when lipids randomly self-assemble into vesicles. Secondly, it is reportedly difficult to immobilize lipid assemblies to surfaces. Third, lipid assemblies are unstable under certain conditions such as elevated temperatures or in the presence of organic solvents.

Significant improvements in the PDA-vesicle system were recently disclosed (Charych et. al. U.S. Pat. No. 6,022,748). By this approach, lipid assemblies were immobilized in sol-gel glasses to create interpenetrating networks of polydiacetylene and alkoxysilane/silicon dioxide domains. The resulting organization helped address some of the problems related to lipid immobilization and instability, but also showed some of its own problems. Primarily, it depends on the formation of a compatible mixture between the lipid-based sensor and a sol-gel precursor, which may not be possible for every type of sensing group formulation. Secondly, incorporation of sol-gel materials adds a significant, new step of synthetic complexity to the practical realization of this invention.

Others have reported the synthesis of crosslinkable dendritic materials containing diacetylene functional groups. For example, in *Colloids and Surfaces A: Physicochemical and Engineering Aspects*, Volume 171, Pages 185–197, (2000), 10,12-pentacosadiynoic acid was attached to the end-groups of generation 2 polyamidoamine (PAMAM) dendrimers, and the resulting amphiphilic multi-arm star polymers were cross-linked as monolayers on the air-water interface or in dilute colloidal suspension. The authors of this study clearly recognized that their system almost certainly did not polymerize intramolecularly, that is, within the confines of a single macromolecule. Further, although they noted previous utilization of polydiacetylenes in sensing applications, they did not indicate that their own work had any potential for chemical or biological sensors. Similarly, in *Polymer Preprints*, Volume 43, Number 2, Page 450 (2002), octadeca-5,7-diyn-1-ol was attached to several small polyamide dendrons and polymerized to insoluble network materials. As in the previous example, the potential sensing applications of these self-assembled dendrons were not discussed. Moreover, when the —$NH_2$ end groups of PAMAM dendrimers or polyamide dendrons are attached to long chain hydrocarbons (i.e., lipids) at close to 100% conversion via amide or carbamate bonds, as in the above literature examples, the resulting amphiphilic dendritic materials are generally highly crystalline, and hence difficult to process into coherent thin films on substrates.

SUMMARY OF THE INVENTION

In a prior disclosure (U.S. 2002/0192843 A1), the entire content of which is incorporated by reference herein, we described soluble dendrimer-based molecular sensors that are intramolecularly polymerized with alternating conjugated double and triple bonds around the surface of dendritic polymer cores. Because they are constructed from covalent chemical bonds rather than by self-assembly, these molecular sensors have comparative advantages of chemical and thermal stability as well as synthetic control over their PDA-liposome counterparts. In the present invention, we take this approach one step further to solid-state, dendritic polymer network-based colorimetric biosensors in which dendritic blocks are intermolecularly linked by alternating conjugated double and triple bonds. In such a configuration, sensing groups are attached either directly to the dendritic network or through a spacer, which may or may not comprise diacetylene or polydiacetylene functional groups.

These and other features, advantages and objects of the present invention will be further understood and appreciated by those skilled in the art by reference to the following specification, claims and appended drawings.

DESCRIPTION OF THE PREFERRED EMBODIMENTS

Figure 2:
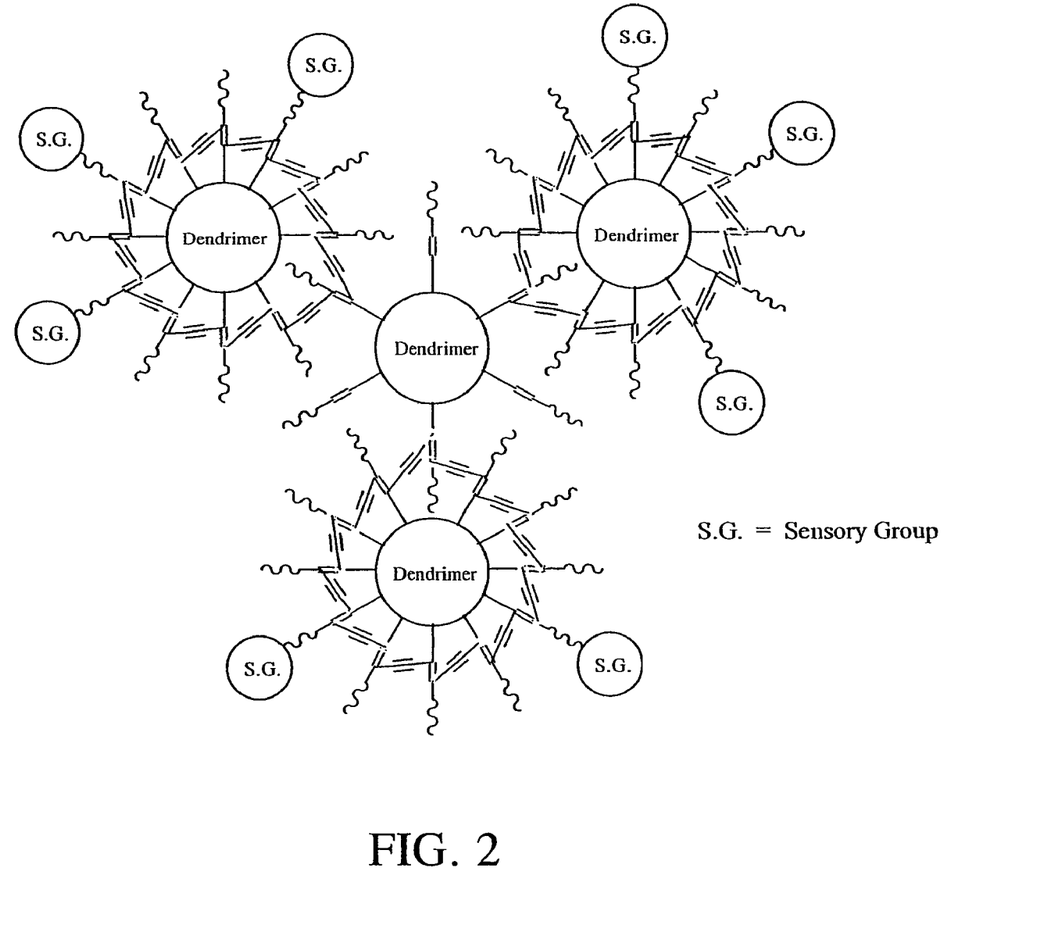
FIG. 2 is a schematic representative of a generalized structure of a dendrimer-based network cross-linked with alternating conjugated double and triple bonds. One or more sensory groups is attached to the dendrimer domains of the network.

The novel macromolecular materials of this invention, which comprise intermolecularly polymerized dendritic networks containing alternating conjugated double and triple bonds, are useful as chemical and/or biological sensors when one or more chemical and/or biological sensory groups are covalently attached to the dendritic building blocks. The materials of this invention my be prepared by reacting dendritic polymers with a compound having a diacetylene moiety to obtain diacetylene functional dendritic polymers, then effecting intermolecular polymerization of the diacetylene moieties. Sensory groups may be attached to the dendritic polymers prior to intermolecular polymerization of the diacetylene moieties. Possible locations for attachment of sensory groups include reactive end-groups of the dendritic polymer, or alternatively the "omega" ends of the "alpha-omega" diacetylene lipids. A schematic representation of a dendritic network sensor with intermolecular polydiacetylene reporter functionality is shown in FIG. 2. The precise location of sensory group attachment is not indicated in this figure.

In this novel approach, dendritic polymer technology imparts precise control of dendrimer sizes, shapes and solubility to the network precursors that is difficult to achieve with other macromolecular architectures. The dendritic polymer cores also preorganize the diacetylene functional groups so that the specific geometric requirements for topochemical polymerization are satisfied, even in a not so highly ordered state as is normally required. If intramolecular polymerization of diacetylene functional groups is desired, as described in our previous disclosure, it is advantageous to use high generation dendrimers (i.e. generation 5 or higher) where end-groups are densely packed together, and hence spatially well-organized, and also to have 100% attachment of diacetylene lipids to these end-groups. It is also advantageous for the diacetylene functional groups to be positioned as close to the point of attachment to the dendrimer core as possible. Conversely, for polydiacetylene networks it is desirable to avoid extremely dense packing of the dendrimer end-groups so that relatively unrestricted intermolecular interpenetration of the dendrimer star arms and subsequent intermolecular polymerization of diacetylene units are facilitated. It is also advantageous for diacetylene functionality to be located near the middle of the lipid chains rather than very close to the point of attachment to the dendritic core.

As in their soluble molecular sensor counterparts, the dendritic networks are stable to elevated temperature and the presence of organic solvents. In the latter, they may swell but will not fall apart or dissolve. The dendritic architecture also imparts a high density of sensing functionality, which promotes high sensitivity to analytes.

Suitable dendritic polymers which may be used include generally any of the known dendritic architectures including dendrimers, tecto-dendrimers, regular dendrons, dendrigrafts, and hyperbranched polymers. Dendritic star-branched polymers having a plurality of arms emanating from a nucleus may also be used. Accordingly, as used herein, dendritic polymers are polymers with densely branched structures having a large number of terminal reactive groups. A dendritic polymer includes several layers or generations of repeating units, usually referred to as branch cells, which all contain one or more branch points. Dendritic polymers, including dendrimers and hyperbranched polymers, are prepared by reaction of monomeric units having two or more reactive groups, or a combination of monomeric units in which at least one of the monomeric units has at least three reactive groups. The dendrimers which can be used include those comprised of a plurality of dendrons that emanate from a common core which can be a single atom or a group of atoms. Each dendron generally consists of terminal surface groups, interior branch junctures having branching functionalities greater than or equal to two, and divalent connectors that covalently connect neighboring branching junctures.

Dendrons and dendrimers can be prepared by convergent or divergent synthesis. Divergent synthesis of dendrons and dendrimers involves a molecular growth process which occurs through a consecutive series of geometrically progressive step-wise additions of branches upon branches in a radially outward molecular direction to produce an ordered arrangement of layered branched cells. Each dendritic macromolecule includes a core cell, one or more layers of interior cells, and an outer layer of surface cells, wherein each of the cells includes a single branch juncture. The cells can be the same or different in chemical structure and branching functionality. The surface branch cells may contain either chemically reactive or passive functional groups. Chemically reactive surface groups can be used for further extension of dendritic growth or for modification of dendritic molecular surfaces. The chemically passive groups may be used to physically modify dendritic surfaces, such as to adjust the ratio of hydrophobic to hydrophilic terminals, and/or to improve the solubility of the dendritic polymer in a particular solvent.

Convergent synthesis of dendrimers and dendrons involves a growth process which begins from what will become the surface of the dendron or dendrimer and progresses in a radial molecular direction toward a focal point or core. In the case of dendrimers, it always ends with an anchoring reaction in which two or more dendrons are connected through their reactive focal points with an anchoring reagent. The dendritic polymers may be ideal or non-ideal, i.e., imperfect or defective. Imperfections are normally a consequence of either incomplete chemical reactions, or competing side reactions. In practice, real dendritic polymers are generally non-ideal, i.e., they contain structural imperfections, which cause the appearance of molecular size distribution.

Hyperbranched polymers represent a class of dendritic polymers which contain higher levels of non-ideal irregular branching as compared to the generally more regular structure of dendrons and dendrimers. Specifically, hyperbranched polymers contain a relatively high number of irregular branches in which not every repeat unit contains a branch juncture. Hence, hyperbranched polymers contain a mixture of linear and fully branched repeating units, whereas an ideal dendrimer contains only fully branched repeating units, and an ideal linear polymer contains only linear repeating units.

The average degree of branching ($\overline{DB}$) may be defined as the number average fraction of branching groups per molecule, i.e., as the ratio of terminal groups plus branch groups to the total number of terminal groups, branch groups, and linear groups as follows:

$$\overline{DB} = \frac{N_t + N_b}{N_t + N_b + N_l}$$

where $N_t$ represents the number of terminal units, $N_b$ represents the number of branched units, and $N_l$ represents the number of linear units. For ideal dendrons and dendrimers this degree of branching is one; for ideal linear polymers it is zero; while for hyperbranched polymers it is greater than zero and less than one, with typical values ranging from about 0.25 to about 0.45.

Dendritic polymers suitable for use with this invention also include macromolecules commonly referred to as cascade molecules, arborols, arborescent grafted molecules, and the like.

They also include hypercomb-branched polymers that comprise non-cross-linked poly-branched polymers prepared by (1) forming a first set of linear polymer branches by initiating polymerization of a first set of monomers which are either protected against or non-reactive to branching and grafting during polymerization, each of the branches having a reactive end group upon completion of polymerization, the reactive end units being incapable of reacting with each other; (2) grafting the branches to a core molecule or core polymer having a plurality of reactive sites capable or reacting with the reactive end groups on the branches; (3) either deprotecting or activating a plurality of monomeric units on each of the branches to create reactive sites; (4) separately forming a second set of linear polymer branches by repeating step (1) with a second set of monomers; (5) attaching the second set of branches to the first set of branches by reacting the reactive end group of the second set of branches with the reactive sites on the first set of branches; and then repeating steps (3), (4) and (5) to add one or more subsequent set of branches.

For purposes of clarifying terminology it should be noted that dendrimers are synthesized by reiterative terminal branching, while hypercomb-branched polymers are synthesized by reiterative comb-branching. In dendrimers, subsequent generations or branches are attached to the terminal moieties of a previous generation, thus limiting the degree of branching to the functionality of the previous generation terminal moiety, which would typically be two or three. In contrast, by branching oligomers upon prior generation oligomer branches, hypercomb-branched polymers having a degree of branching which increases or varies from one generation to the next is possible.

Other suitable classes of dendritic polymers include various combinations of linked dendrimers, such as bridged dendritic polymers and/or dendritic polymer clusters wherein two or more dendritic polymer molecules are covalently bonded together through their reactive terminal groups (either directly or through a linking molecule such as an alpha,omega-telechelic linear oligomer/polymer or other difunctional or polyfunctional molecule), dendritic polymer chains, dendritic polymer networks (e.g., cross-linked dendritic polymers, and core-shell tecto-dendrimers (i.e., a composition comprising a single dendritic core polymer surrounded by a plurality of dendritic shell polymer molecules, each of which is chemically bonded to the surface of the core polymer molecule), or as pendant groups attached to a linear polymer (possibly conjugated).

Methods of preparing and characterizing dendrimers, dendrons, hyperbranched polymers, star-branched polymers, dense star-branched polymers and hypercomb-branched polymers are all well known in the art and thoroughly described in the literature.

Specific examples of dendritic polymers that may be used include polyamidoamine (PAMAM) dendrimers, dendrigrafts and hyperbranched polymers; poly(benzylether) dendrimers, dendrigrafts and hyperbranched polymers; polyester dendrimers and hyperbranched polymers; poly (propyleneimine) (PPI) dendrimers, dendrigrafts and hyperbranched polymers; organosilicon-containing dendrimers, dendrigrafts and hyperbranched polymers, polystyrene arborescent polymers, etc.

Generally, any dendritic polymer (i.e., any polymer having branches upon branches) may be used with this invention, with selection depending on factors such as cost, availability, solubility, and terminal functional group reactivity and density. Obviously, lower cost materials and commercially available materials are preferred when other factors such as solubility, terminal functional group reactivity and density are equal. Solubility may or may not be an important factor, depending upon the particular application in which the macromolecular compounds of this invention are used. However, in many cases, it may be desirable to use a dendritic polymer that is soluble in water, oil, or a particular solvent. In general, to provide the highest degree of sensor sensitivity, as manifested by an observable color change upon contact with a medium containing an analyte, dendritic polymers with a high density of sensing functionality are preferred. In general, this means that dendritic polymers having a high density of terminal functional groups are preferred for preparing the colorimetric macromolecules of this invention.

Examples of terminal functional groups that may be present on the dendritic polymer used for preparing the colorimetric macromolecules of this invention include hydroxy, mercapto, carboxyl, ester, alkoxy, alkenyl, allyl, vinyl, amino, halo, urea, oxiranyl, aziridinyl, oxazolinyl, imidazolinyl, sulfonato, phosphonato, hydrosilyl, isocyanato, isothiocyanato, etc. Various known chemistries are useable with these and other surface functional groups for attachment of the colorimetric reagent to the dendritic polymer core.

The colorimetric reagent may comprise any compound or compounds that can be covalently bonded to the terminal functional groups of the dendritic polymer molecule and subsequently reacted to achieve intermolecular cross-linking through segments containing alternating conjugated double and triple bonds, i.e., —C=C—C≡C— repeating units.

Examples include diacetylenes such as 5,7-docosadiynoic acid, 10,12-pentacosadiynoic acid, 5,7-pentacosadiynoic acid, and combinations thereof. A variety of diacetylenic lipids are commercially available, but they can also be synthesized using the well known Cadiot-Chodkiewicz acetylene coupling reaction.

If the above mentioned diacetylenes do not undergo topochemical polymerization reaction, they may exhibit photoluminescent activity in their own right, which makes them suitable for potential detection of chemical and/or biological analytes. The diacetylene compounds may include only one terminal functional group that is reactive with a terminal functional group on the dendritic polymer. Alternatively, the diacetylene compounds used for preparing the colorimetric chemical and/or biological sensors of this invention may have two terminal functional groups at opposite ends of the diacetylene reagent, one selected to react with the terminal functional groups of the dendritic polymer, and another that binds to a ligand sensory group.

The spatial arrangement of the diacetylene moieties is strongly influenced by their position in the lipid chains as well as by the choice of dendrimer generation. Therefore, the length of spacers can be adjusted to promote intermolecular cross-linking and suppress intramolecular polymerization of the diacetylene moieties. More specifically, diacetylene-containing lipid chains having longer spacer moieties that increase the distance between adjacent diacetylene moieties in a diacetylene functionalized dendritic polymer favor intermolecular cross-linking and suppress intramolecular polymerization of the diacetylene moieties. Desirably, the spacer moiety between the point of attachment to the dendritic polymer and diacetylene moiety will have at least 5 and preferably more atoms in a linear chain.

In order to further favor intermolecular cross-linking of the diacetylene moieties and prevent their intramolecular polymerization, the reaction is preferably carried out as a cast film in the solid state.

The choice of sensory groups will depend on the identity of the targeted chemical or biological analyte and on the type of binding desired (i.e., large verses small analyte; specific binding verses non-specific binding, etc.). The sensory groups of the present invention can be selected from a wide variety of moieties having an affinity for the analyte of choice, and may be of a broad range, such as when a class of materials is to be assayed.

Examples of sensory groups that may be used include, but are not limited to, peptides, carbohydrates, nucleic acids, biotin, histamine drugs, chromophores, antigens, chelating compounds, molecular recognition complexes, ionic groups, polymerizable groups, linker groups, electron donors, electron acceptors, hydrophobic groups, hydrophilic groups, receptor binding groups, antibodies, and other organic molecules which bind to receptors, as well as combinations thereof.

As previously stated, the diacetylene-containing lipid chains used for preparing the diacetylene functionalized dendritic polymers may have only one terminal functional group for attachment to a terminal functional group on the dendritic polymer, or two terminal functional groups, one for attachment to a terminal functional group on the dendritic polymer and one for attachment of a sensory group. When a monofunctional diacetylene-containing lipid chain is employed, sensory groups can be bonded directly to the dendritic polymer. A dendritic polymer having two different types of terminal functional groups may be employed to control the relative proportion or spacial distribution of diacetylene-containing functional groups to sensory functional groups on the dendritic polymer. When a difunctional diacetylene-containing lipid chain is employed, the sensory groups may be bonded to the free terminal functional group at the end of the diacetylene-containing lipid chain. Alternatively, the sensory groups may be pre-reacted with a difunctional diacetylene-containing lipid chain to form a monofunctional diacetylene-containing lipid chain having a sensory group on one end and a functional group that is reactive with a functional group of the dendritic polymer on the other end.

In one embodiment of this invention, the dendritic polymers are polyamidoamine (PAMAM) dendrimers that have a predetermined statistical mixture of two or more end-groups with different chemical reactivity, such as hydroxyl (OH) and amine ($NH_2$) units. Differing reactivity of these functional groups allows selective covalent attachment of diacetylene lipids to some or all of the amine end-groups, while leaving all of the relatively less reactive hydroxyls unaffected. As a consequence, the diacetylene functional groups are preferentially attached via amide linkages, which preferably organize polymerizable functional groups in preparation for intermolecular network formation. The presence of unmodified hydroxyl end-groups creates a moderate degree of disorder, hence improving the solubility of diacetylene dendrimer network precursors prior to intermolecular polymerization. Sufficient microcrystalline order remains, however, such that geometrically constrained topochemical polymerization may occur. Additionally, the reduced crystallinity of these materials facilities deposition of coherent films on a variety of substrates such as glass, quartz, silicon, paper, plastic, cellulose and nitrocellulose.

When lipids are covalently attached to PAMAM dendrimers via amide linkages, the resulting amphiphilic star-shaped macromolecules exhibit poor solubility in a wide variety of single-component solvents. Further, we have found that optimal solubility of these star polymers is usually achieved in binary mixtures of high and low polarity solvents, such as methanol and chloroform. This behavior is believed to result from nanophase separation between their hydrophilic PAMAM dendritic nuclei and oleophilic lipid arms, wherein the latter are attracted to each other by a combination of Van der Waals interactions between their hydrocarbon segments and hydrogen bonding interactions between the amide linkages.

In one aspect of the invention, problems with poor solubility and excessive crystallinity of these multi-arm star polymers are solved through use of mixed surface PAMAM dendrimers with predetermined mixtures of two or more different kinds of end-groups (e.g., hydroxyl and amine). Lipids activated by electrophilic N-hydroxysuccinimidyl ester functional groups react rapidly with primary amines and more slowly with hydroxyl units (see FIGS. 3 and 4 for examples). Hence, on a usual synthetic time scale of 1–48 hours, only the amine end groups of the PAMAMs react with the diacetylene lipids, and the presence of unreacted hydroxyl end-groups imparts better solubility to the sensing ensembles prior to polymerization.

Figure 3:
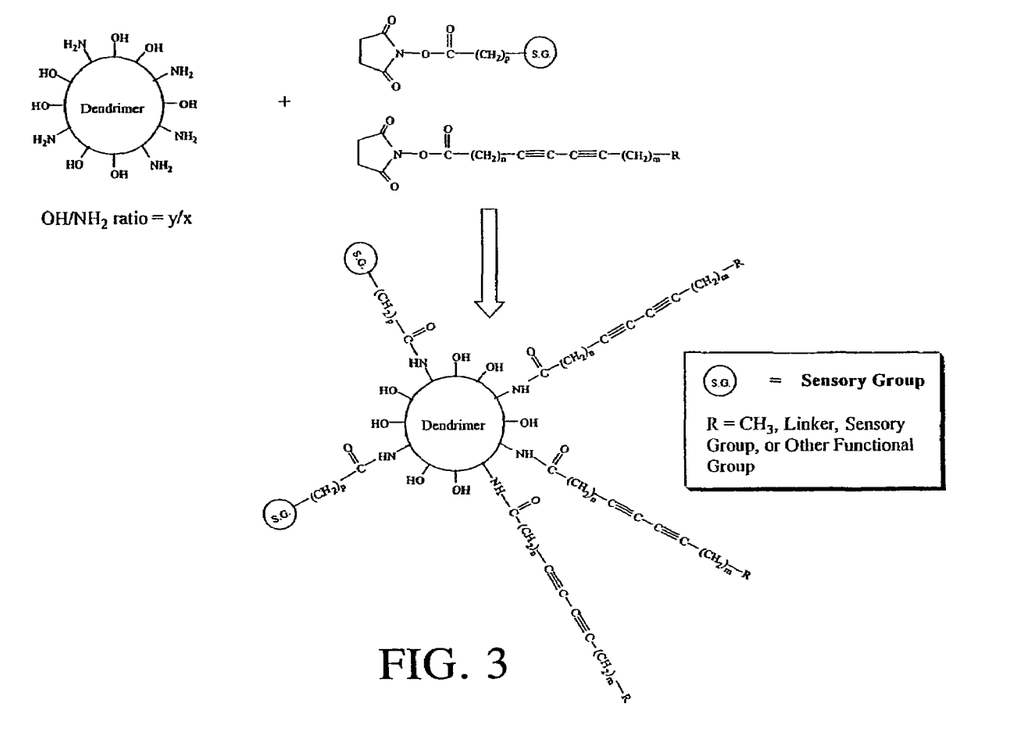
FIG. 3 is a schematic representation of a soluble dendritic star precursor to the network polymer sensor depicted in FIG. 2. In this structure sensing groups are attached to some of the dendrimer $NH_2$ end-groups and diacetylene lipid arms are attached to the remainder of the $NH_2$ end-groups. The —OH end groups of the dendritic polymer do not react under the conditions used.

In one embodiment of the invention, diacetylene lipids and sensing groups are both covalently attached to the amine end-groups of the dendrimer cores (FIG. 3). The number of diacetylene lipids attached to the dendritic template must be above a certain threshold for successful intermolecular polymerization. This threshold is believed to be about 10–20% of the initial dendrimer end groups present.

Figure 4:
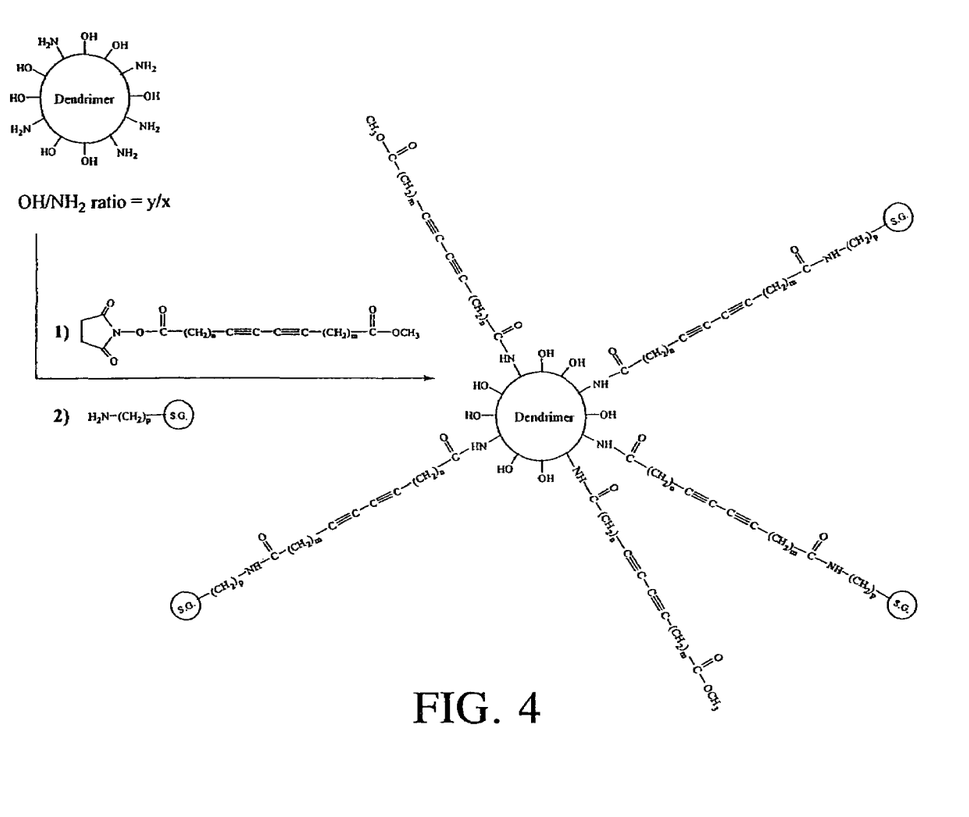
FIG. 4 is a schematic representation of another soluble dendritic star precursor to the network polymer sensor depicted in FIG. 2. In this example the sensing groups are attached to some or all of the end-groups of the diacetylene lipid arms. The —OH end groups of the dendritic polymer do not react under the conditions used.

In another embodiment, diacetylene lipids are covalently attached to all of the amine end groups, and sensing groups are covalently attached to the "omega" ends of some or all of the diacetylene lipids. A plausible approach to this embodiment is shown in FIG. 4, where an "alpha-omega" diacetylene lipid has activated succinimide ester functionality on one end ("alpha") and less reactive methyl ester functionality on the other end ("omega"). After the lipid is attached to the dendrimer by the reactive succinimide ester end, a sensory group containing reactive primary amine functionality is attached to the lipid through reaction at the methyl ester end.

The network polymers of this invention may be used either as stand-alone materials, or they can be immobilized on solid substrates such as glass, silica gel, silicon, paper, plastic, nitrocellulose, quartz, metal, wood and cellulose.

EXAMPLES

Example 1

Sequential attachment of biotin and 10,12-pentacosadiynoic acid to the amine end groups of a generation 4 PAMAM dendrimer that contains a statistical mixture of amine and hydroxyl end groups (52% $NH_2$ & 48% OH).

0.39 g of a 42.55 weight % solution of generation 4 PAMAM dendrimer containing 52% amine and 48% hydroxyl end groups (0.16 g, 0.37 mmol of —$NH_2$ groups) was slowly added to a stirred mixture of N-succinimidyl-biotin (0.060 g, 0.18 mmol) in 10 ml methanol. The reaction mixture was stirred for 3 days. A solution of N-succinimidyl-10,12-pentacosadiynoic acid (0.108 g, 0.23 mmol) in 5 ml methylene chloride was subsequently added to the reaction mixture, which was then stirred for an additional three days to ensure complete reaction with all remaining amine end groups. The reaction mixture was concentrated on a rotary evaporator and purified by ultrafiltration in methanol. The solvent was removed on a rotary evaporator, and the obtained modified dendrimer was dried by lyophilization under vacuum. NMR characterization indicated that approximately 30% of the —$NH_2$ end-groups were substituted with biotin. $^1$H NMR in DMSO-$d_6$: 7.95 (s, [—CON H$CH_2CH_2$N=]), 7.83 (s, [—CONHCH$_2$CH$_2$N=]), 6.41 (d, [—NHCONH—]), 5.91 (d, [—NHCONH—]), 4.30 (s, [—C HCH—]), 4.15, (s, [—CHCH—]), 3.39 (t, [—CONHCH$_2$C H$_2$OH]), 3.08 (m, [—CONHCH$_2$CH$_2$N=]), 2.65 (b, s, [=NCH$_2$CH$_2$CONH—]), 2.51–2.46 (m, [—CONHCH$_2$CH $_2$N=]), 2.25–2.21 (m, [=NCH$_2$CH$_2$CONH—]), 2.04 (t, [—CH$_2$CCCCCH$_2$—]), 1.614 (b, t), 1.43 (b, t), 1.23 (s), 0.97 (t, [—CH$_3$]), 0.85 (t, [—CH$_3$]). $^{13}$C{$^1$H} NMR in CD$_3$OD: 176.57 (—NHCH$_2$CH$_2$NHCOC$_{25}$H$_{41}$), 175.21(s, —CONHCH$_2$CH$_2$N=), 174.80 (s, —CONHCH$_2$CH$_2$N=), 78.18(s, [—CH$_2$CCCCH$_2$—]), 66.72 (s, [—CH$_2$C CCCCH$_2$—]), 63.56 (s), 61.94 (s, [—CONHCH$_2$CH$_2$ OH]), 57.04 (s), 53.86 (s, [—CONHCH$_2$CH$_2$N=]), 51.41 (s, [=N CH$_2$CH$_2$CONH—]), 43.95 (s), 43.27 (s, [—CONH CH$_2$CH$_2$OH]), 40.37 (s), 38.85 (s, [—CONH CH$_2$CH$_2$N=]), 37.90 (s), 37.43 (s), 36.06 (s), 34.98 (s, [=NCH$_2$CH$_2$CONH—]), 33.19 (s), 30.80–29.73 (m), 27.60 (s),27.09 (s), 23.85 (s), 19.97 (s), 15.79 (, —CH$_3$), 14.62 (s, —CH$_3$). IR on NaCl plate (selected peaks); 3263 cm−1 [v(—NH)]; 1650 cm [strong, v(C=O)]; 1547 cm [strong, v(CNH) of amide].

Example 2

Detection of Avidin [Neogen Experiment, Jul. 26, 2002]

A dilute methanol solution of the biotin/10,12-pentacosadiynoic acid/G4 PAMAM dendrimer of Example 1 was spotted on filter paper (5×10 µL). After each application the solvent was evaporated. The filter paper was irradiated with a UV lamp (245 nm, 6 W) from 20 cm distance for 30 to 60 seconds, resulting in a violet-blue colored spot. 10 µL of a 1 mg/mL solution of streptavidin was added to the blue spot, which caused the color to shift from violet-blue to faint red.

As a simple control experiment, pure water was added to the blue spot on the filter paper, which resulted in no observable change in color.

In a related control experiment, the dilute methanol solution of the biotin/10,12-pentacosadiynoic acid/G4 PAMAM dendrimer was spotted on filter paper (5×10 µL) and dried after each application. 10 µL of a 1 mg/mL solution of streptavidin was then added to the spot followed by drying and irradiation with the UV lamp. This time the spot on the filter paper remained colorless, indicating strong influence of biotin-avidin binding before or after polymerization of the diacetylene functional groups.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A compound comprising dendritic polymer moieties linked to one another by a moiety having alternating conjugated double and triple bonds, and at least one sensory group bonded to the compound, the dendritic polymer moieties having at least two different types of reactive and/or reacted end-groups.

2. A compound of claim 1 in which the dendritic polymer moieties have —OH end-groups, and —$NH_2$ end-groups and/or reacted moieties of —$NH_2$ end-groups.

3. A compound of claim 2 in which the dendritic polymer moieties are polyamidoamine (PAMAM) dendrimer moieties.

4. A compound of claim 2 in which the PAMAM dendrimer moieties have 25% —$NH_2$ end-groups and/or reacted moieties of —$NH_2$ end-groups, and 75% —OH end-groups.

5. A compound of claim 1, wherein the sensory group is selected from the group consisting of peptides, carbohydrates, nucleic acids, biotin, avidin, histamine, chromophores, antigens, antibodies, enzymes, chelating compounds, molecular recognition complexes, ionic groups, polymerizable groups, linker groups, electron donors, electron acceptors, hydrophobic groups, hydrophulic groups, receptor binding groups, antibodies, and combinations thereof.

6. A compound of claim 1, wherein the alternating conjugated double and triple bonds are formed by polymerization of diacetylene-functionalized dendritic polymers.

7. A compound of claim 6, wherein the dendritic polymer is a dendrimer.

8. A compound of claim 6, wherein the dendritic polymer is a hyperbranched polymer.

9. A compound of claim 6, wherein the dendritic polymer is a hyperbranched polymer having an average degree of branching from about 0.25 to about 0.45.

10. A compound of claim 6, wherein the dendritic polymer is a dendron.

11. A compound of claim 6, wherein the dendritic polymer is a dendrigraft.

12. A compound of claim 6, wherein the dendritic polymer is a dendronized linear polymer.

13. A compound of claim 6, wherein the dendritic polymer is a tecto-dendrinier.

14. A compound of claim 1, wherein the sensory group is attached directly to a dendritic polymer block of the cross-linked material.

15. A compound of claim 1, wherein the sensory group is attached to a dendritic polymer block of the cross-linked material through a spacer.

16. A compound of claim 15 wherein the spacer through which the sensory group is attached to the dendritic segment comprises a diacetylene or polydiacetylene moiety.

17. A diacetylene functionalized dendritic compound obtained by reaction of a dendritic polymer having at least two different types of reactive end-groups with a diacetylene reagent having the following general formula:

wherein X is a group that reacts with one or more end groups of the dendritic polymer; R is a sensory group; and n and m are integers.

18. A compound of claim 17 in which X is Cl—, Br—, I—, p-tosyl, mesyl, acryloxy, isocyanato, epoxy, $CH_3OC(O)$—, $ClC(O)$—, N-hydroxysuccinimidyl-C(O)—, pentafluorophenoxy-C(O)— or p-nitrophenoxy-C(O)—.

19. A compound of claim 17 in which n is 0 to 25.

20. A compound of claim 17 in which m is 0 to 25.

21. A compound of claim 17 in which one of the at least two different types of reactive end-groups are —$NH_2$ end-groups.

22. A method of detecting and/or quantifying the amount of an analyte in a sample, comprising:
    contacting a sample that is to be analyzed for a particular analyte with the compound of claim 1;
    allowing specific binding between the analyte and the sensory group;
    monitoring a detectable change caused by specific binding between the analyte and the sensory group; and
    correlating the detectable change with the presence of an analyte in the sample, and optionally correlating the detectable change with an amount of analyte present in the sample.

23. The method of claim 22 where the sensing material is imbedded in or deposited on a solid substrate.

24. The method of claim 23 where the substrate is glass, quartz, silicon, other metals, wood, plastic, paper, cellulose or nitrocellulose.

25. The method of claim 22 in which detection is achieved by means of a visible color change.

26. The method of claim 22 in which quantitative detection is achieved by means of a color change measured with an ultraviolet/visible spectrometer.

27. The method of claim 22 in which detection is achieved by means of a change in fluorescent properties.

* * * * *